(12) United States Patent
Farkas et al.

(10) Patent No.: US 7,137,983 B2
(45) Date of Patent: Nov. 21, 2006

(54) SET OF SURGICAL INSTRUMENTS FOR THE FIXATION OF VERTEBRAE

(75) Inventors: József Farkas, Eger (HU); Péter Pál Varga, Budapest (HU)

(73) Assignee: Sanatmetal KFT, Eger (HU)

( * ) Notice: Subject to any disclaimer, the term of this patent is extended or adjusted under 35 U.S.C. 154(b) by 51 days.

(21) Appl. No.: 10/432,561

(22) PCT Filed: Nov. 16, 2001

(86) PCT No.: PCT/HU01/00115

§ 371 (c)(1),
(2), (4) Date: May 22, 2003

(87) PCT Pub. No.: WO2002/041797

PCT Pub. Date: May 30, 2005

(65) Prior Publication Data

US 2004/0015167 A1    Jan. 22, 2004

(30) Foreign Application Priority Data

Nov. 22, 2000  (HU) .................................. 0004670

(51) Int. Cl.
*A61B 17/56* (2006.01)
*A61F 2/30* (2006.01)
(52) U.S. Cl. .................. 606/61; 606/72; 606/73
(58) Field of Classification Search .............. 606/60, 606/61, 72, 73, 62, 65
See application file for complete search history.

(56) References Cited

U.S. PATENT DOCUMENTS

| 4,697,582 | A | * | 10/1987 | William ................. 606/61 |
| 5,067,955 | A | * | 11/1991 | Cotrel .................. 606/61 |
| 5,603,714 | A | * | 2/1997 | Kaneda et al. ........... 606/61 |
| 6,074,393 | A | * | 6/2000 | Sitoto .................. 606/73 |
| 6,821,277 | B1 | * | 11/2004 | Teitelbaum ............. 606/61 |

FOREIGN PATENT DOCUMENTS

| FR | 2702363 |   | 9/1994 |        |
| FR | 2745706 |   | 9/1997 |        |
| GB | 2294394 | * | 1/1996 | 606/61 |
| GB | 2294394 |   | 5/1996 |        |

* cited by examiner

*Primary Examiner*—Pedro Philogene
(74) *Attorney, Agent, or Firm*—Joseph G. Seeber

(57) ABSTRACT

A set of surgical instruments for the fusion of vertebrae contains supporting elements that have a threaded stem that can be screwed into the vertebra and a head part positioned at the outer end of the threaded stem. A connection unit is fitted between the supporting elements and a fixating device serving to brace together the supporting elements and the connection unit, and the head part of the supporting element has an accepting opening suitable for joining the connecting unit. The accepting opening is formed by the unification of an introductory cleft running from the outer surface of the head part and penetrating into the head part, and a lead-through seat that forms the continuation of the introductory cleft, is worked into the head part and bells out from there. The head part has a fusion opening that has a first connection piece and ends in the lead-through seat, and the fixating device has a tightening body that is positioned in the fusion opening so that it may move. A second connecting piece operates in unison with the first connecting piece, and the connecting unit is assembled from the group of the elemental connection strands penetrating the introductory cleft of the head part.

16 Claims, 1 Drawing Sheet

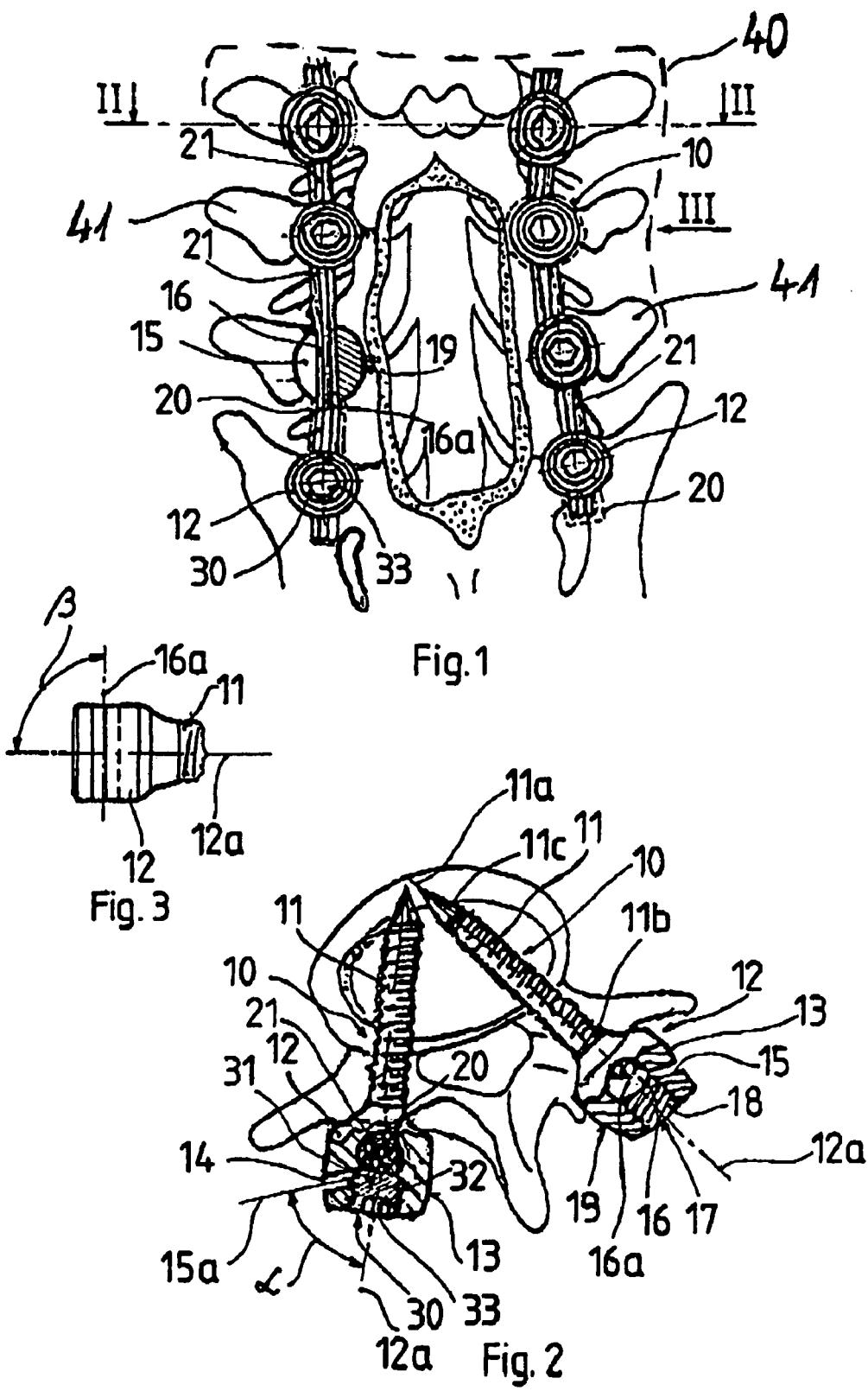

SET OF SURGICAL INSTRUMENTS FOR THE FIXATION OF VERTEBRAE

TECHNICAL FIELD

The subject of the invention relates to a set of surgical instruments designed for fixating or fusing spinal vertebrae. The instruments include supporting elements having a threaded rod or stem that can be screwed into the vertebra and a head part or unit positioned at the top or outer end of the threaded rod or stem, a connecting unit that is fitted between the supporting elements, and a fixating device serving to brace together the supporting elements and the connecting unit. The head part or unit of the supporting element has an accepting opening suitable for joining the connecting unit. The accepting opening is formed by the unification of the introductory cleft running from the outer surface of the head part or unit and penetrating into the head part or unit. A lead-through seat forms the continuation of the introductory cleft, is worked into the head part or unit, and bells out from there. Furthermore, the head part or unit has a fusion opening that has a first connection piece and ends in the lead-through seat, and the fixating device has a tightening body which is positioned in the fusion opening so that it may move, and which has a second connecting piece that operates in unison with the first connecting piece.

RELATED ART

Numerous vertebral fusion implants are used today in spine surgery. The essence of most is that the supporting elements that can be screwed into the vertebrae are connected to each other with connecting bodies, which are then unified with the help of fixating devices into a load transfer structure. Such solutions can be seen in, among others, such literature as HU T/63.548 and HU T/58.496, and in patent description No. HU 209.422.

The disadvantage of the known solutions, however, is that the longitudinal sizes of the usual supporting elements and the fixating devices are complex and, due to the structure that results in significant dimensions, the operation is more difficult and the "hiding" of the built-in structural elements cannot be solved in every case.

Another disadvantage is that, with the traditional assemblies, where the elements are rigid, when the patient moves, the supporting elements may become deformed or, in extreme cases, broken at which time the fixation of the vertebra is terminated. The restoration of the desired condition may only be solved with a further operation that causes a significant burden for the patient.

A further deficiency of the known versions is that the normally used screw fixating connection device is susceptible to fatigue, and the replacement of the faulty element and the correction of the fixture also require a further surgical intervention.

Another unfavourable aspect is that, in the case of spine implants that bridge over more than two vertebrae, the appropriate planar and spatial connections of the supporting elements and connection bodies cause great difficulty, require a great number of special instruments and auxiliary equipment, and also significantly increase the duration of the operation, which not only increases the burden on the patient, but also unjustifiably increases the possibility of complications during the operation.

A further aspect that has to be treated as a disadvantage is that, in the case of traditional solutions in different sections of the spinal column, supporting elements of differing sizes and different instruments have to be used, which makes the fast and efficient performance of the operation even more difficult.

U.S. Pat. No. 5,603,714 discloses a set of equipment in which the supporting element fixed to the bone has a cleft worked into it in the head-part that protrudes out of the bone, which cleft leads to an accepting seat. Through this cleft, the connection part-unit that fixes together the individual supporting elements can be placed into the accepting seat.

The significant disadvantage of this structure, however, is that the dimensions of the accepting seat, of the cleft leading to it, and of the connection part-unit are essentially equal, and so only a single, thick cross-section, less deformable, rod-like connection unit can be fixed into the head part of the supporting element. Such a connection system does not provide a sufficiently flexible connection possibility between the supporting elements.

Another disadvantage is that, due to the geometric dimensions of the head part of the supporting element presented above, the connection part-unit is difficult to handle and is difficult to fix into the accepting seat of the head part. As an example, after threading a not-so-flexible connection part-unit with a cross-section comparable to the size of the accepting seat through the cleft, if it is decided not to use the fixing body immediately, the connection part-unit may relatively easily pop out of the accepting seat. Therefore, the connection part-unit has to be fixed into the head part of the supporting element immediately following positioning, which, however, makes the fine setting of the connection part-unit and the positioning of the supporting elements more complicated.

French Patent FR 2.702.363 discloses a connection part-unit in which several connection wires with a small cross-section are held together as a single rod. The advantage of this arrangement is that the deformation ability of the strands is greater, and so, from the point of view of shape formation, the connection part-unit has more favourable characteristics.

However, a significant disadvantage is that, due to the fixing together of the wires, putting them into the supporting elements and fixing them is complex since, due to the joint movement of the wires here also, the cleft leading into the fixing hollow essentially has to comply with the cross-section size formed by the wires altogether. As a result of this, this arrangement also does not solve the problem of easy handling and simpler fixing.

British Patent GB 2.294.394. presents a solution where the bundle of elemental strands, pre-bent to a determined form, forms the connection part-unit, while on the head part of the screws to be fixed into the vertebrae, there is a wide cleft to receive these elemental strands. An internal screw may be placed in the cleft, which keeps the elemental strands in the cleft. During the assembly of the structure, all of the elements of the connection part-unit have to be used, and so only one device containing six fixing screws, and suitable for the linking of three neighbouring vertebrae, can be set up. The flexible elemental strands fog the connection part-unit can be placed into the cleft after the removal of the internal screw in the head of the fixing screw, and the internal screw may only be replaced in the head of the fixing screw after all of the elemental strands to be put into the cleft have been positioned.

The greatest disadvantage of the above solution is that, due to the compulsory use of the six fixing screws and the pre-shaped, bent linking and clamping elemental strands, it can only be used in certain cases and in the case of the linking together of a restricted number of vertebrae. Therefore, its area of use is significantly limited, and it is not suitable for carrying out general vertebrae fixing tasks. Because of the elemental strands bent into a "U" shape, which realise the link between the two screws of the fixing screw pairs that are screwed into the one vertebrae, the solution can only be properly used if the fixing screws are able to be screwed into the body of the vertebrae precisely conforming to the geometric size of the "U" shape. However, this gives an almost impossible task to the operator due to the unique bone structure of the individual. The other possibility would be one in which the elemental strands bent in a "U" shape were made in innumerable sizes, which would require an unjustifiably large number of components and an extensive set. Due to these significant disadvantages, this solution has not become widespread.

Another disadvantage is that all of the pre-bent elemental strands are to be used during the fixing, so that a flexible fix adapting to the patient's form and loading cannot be set up.

A significant disadvantage is that keeping the elemental strands of the connection part-unit in the seating that goes through the head part is difficult due to the outward-facing, wide cleft, which makes the job of the operator significantly more difficult, and which may increase the duration of the operation to a large extent, which is unfavourable from the point of view of the patient. The pre-formed elemental strands connecting the six fixing screws to each other cannot be kept in the wide cleft so that they remain in the expected position without any further support. There is no possibility of such help due to the small area of the operation and the circumstances that present themselves during surgery, e.g. bleeding and reducing bleeding.

Another disadvantage that can be listed here is that the fixing of the fixing screws is in every case determined by the form and size of the vertebrae, so that, in general, the six fixing screws become positioned at varying heights and angles. As a result, the elemental strands need to be bent to conform with these essentially completely irregularly arranged clefts, and then, after they have been fitted into the wide clefts, they are left to themselves. In practice, this cannot be solved.

Another significant disadvantage is that the elements carrying out the cross-linking between the fixing screws result in such rigidity that, in the case of porous vertebrae, this can in some cases lead to the pulling out of the fixing screw.

A further disadvantage of the wide and deep straight cleft forming the seating leading through the head part is that, on the one hand, it increases the dimensions of the head part, which may be a source of further accidents following the operation, and, on the other hand, it reduces the solidity of the head part, which provides an unjustified restriction on occurring loads.

DISCLOSURE OF INVENTION

With the creation of the surgical instruments disclosed herein, the aim was to overcome the faults of the known versions and to create a construction with the help of which, in a short operation time and using a small number of components, one could realize vertebral fusion that would be more stable and more durable than that achieved by the known methods with respect to any section of the spinal column, independent of the location of the injury.

The basic idea of the invention was formed by the recognition that, if screws with formed heads and unique geometry are used and the connection unit is formed innovatively by a group of flexible strands that are easily deformed on their own, and that can be handled individually and grouped in the desired amount, then the task can be solved. During experiments, it was realised that, if the thin strands that can be easily formed on their own are bound together in an appropriately formed head in a new way, then they, together, may form a sufficiently rigid connection part, ruling out deformation and fatigue.

In accordance with the set aim, the set of surgical instruments for the fusion of vertebrae according to the invention contains supporting elements that have a threaded stem that can be screwed into the vertebra and a head part positioned at the outer end of the threaded stem, a connecting unit that is fitted between the supporting elements, and a fixing device serving to brace together the supporting elements and the connecting unit. The head part of the supporting element has an accepting opening suitable for connecting the connecting unit. The invention is constructed in such a way that the accepting opening is formed by the unification of the introductory cleft running from the outer surface of the head part and penetrating into the head part and the lead-through seat that forms the continuation of the introductory cleft and is worked into the head part and that bells out from there. Furthermore, the head part has a fusion opening that has a first connection piece and ends in the lead through seat, the fixating device has a tightening body that is positioned in the fusion opening so that it may move, and that has a second connection piece that operates in unison with the first connection piece. The connecting unit is assembled from the group of the elemental connection strands that can be moved independently of each other on the introductory cleft of the head part, and pushed through individually. The introductory cleft has a width suitable for the penetration of a single elemental connection strand, while the lead-through seat has a splayed out cross-section suitable for the simultaneous acceptance of several elemental connection strands.

A further criterion of the instrumentation according to the invention is that the longitudinal axis of the threaded stem and the main axis of the head part are coaxially positioned.

In a possible version of the instruments, the main axis of the head part is at an angle in the range of 10–120° with the main plane of the introductory cleft, while the leading lead through seat's axis of symmetry and the main axis of the head part are at an angle in the range of 50–130° with respect to one another.

In a further different form of the invention, on the outside surface of the head part, there are one or more flat areas.

A favourable aspect from the point of view of the instruments may be that the elemental connection strands are made of flexible material that is able to deform, for example, metal such as very high purity steel wire or titanium alloy.

The instruments according to the invention have numerous advantageous features. The most important of these is that, with the use of the supporting elements that have a uniquely formed head part or unit and the novel connecting unit, the approach for the surgery can be significantly reduced and can be carried out quickly using simpler instruments, with the use of few components and auxiliary equipment and without especially burdening the patient. This significantly reduces the operation burden and the danger of possible complications, and greatly aids the faster recovery of the patient.

Another advantage is that the components that are different from those traditionally used may be used along the whole length of the spinal column, both in the dorsal and lumbar sections. Moreover, a system may be set up that is not overly rigid and is formed according to the patient's build and the type of injury.

Also favourable is that, in addition to the easy formability of the elemental connection strands, the whole connecting unit has the required amount of rigidity and is still more flexible than the traditional bridging elements, so that deformation, breakage or fatigue will not occur in the case of any single component. This further reduces risk following the operation.

Still another advantage is that the elements of the instruments may be easily manufactured, easily handled and sterilised.

BRIEF DESCRIPTION OF DRAWINGS

The invention will be described in detail in accordance with the following construction example and the accompanying drawings, in which:

FIG. 1 is a top view of the instruments according to the invention,

FIG. 2 is a cross section view taken along the plane II—II in FIG. 1, and

FIG. 3 is a detailed view taken from the direction marked III in FIG. 1.

DETAILED DESCRIPTION

FIG. 1 shows the surgical instrument set according to the invention built into the vertebrae 41 of the spinal column 40 in an assembled state. It can be easily seen that each one of the supporting elements 10 is fixed into a separate vertebra 41 so that the head parts 12 protrude out of the vertebrae 41. The supporting elements 10 are positioned so that the axes of symmetry 16a of the lead-through seats 16 in the head parts 12 fall in the longitudinal direction of the spinal column 40. The elemental connection strands 21 are in the lead-through seats 16 of the head parts 12 of the supporting elements 10, with elemental connection strands 21 together forming the connecting unit 20. The connecting unit 20 assembled from the elemental connection strands 21 is held in the lead-through seats 16 of the head parts 12 by the tightening bodies 31 (see FIG. 2) of the fixating devices 30. The tightening bodies 31 of the fixating devices 30 have a connector piece 33, with the help of which the tightening bodies 31 are screwed into the head part 12.

In FIG. 2, the connection of the tightening body 31 of the fixating device 30 with the head part 12 of the supporting element 10 can be easily seen, as can the structure of the supporting element 10. Apart from the head part 12, the supporting element 10 also includes a threaded stem 11. The head part 12 is positioned in the continuation of the outer end 11b of the threaded stem 11 in such a way that the main axis 12a of the head part 12 and the longitudinal axis 11a of the threaded stem 11 are coaxial. The inner end 11c of the threaded stem 11 opposite the head part 12 is pointed, which facilitates positioning in the vertebra 41. The lead-through seat 16 of the head part 12 is connected to the introductory cleft 15, which introductory cleft 15 opens out to the outer surface 13 of the head part 12, and its purpose is to make the fitting of the elemental connection strands 21 into the lead-through seat 16 simple. The lead-through seat 16 and the introductory cleft 15 together form the accepting opening 14. In this case, the outer surface 13 of the head part 12 is in the form of a cylindrical shell, and the surface area opposite the introductory cleft 15 has a flat area 19. The flat area 19 facilitates the screwing of the supporting element 10 into the vertebra 41.

In FIG. 2, it may also be observed that the main plane 15a of the introductory cleft 15 and the main axis 12a of the head part 12 are at an angle "α" with respect to each other, that angle being in the range of 10–120°, which in the present example preferably falls in the range of 70–80°.

FIG. 3 illustrates that the axis of symmetry 16a of the lead-through seat 16 and the main axis 12a of the head part 12 are at an angle in the range of 50–130° relative to one another, which in the present case is preferably an angle "β" of 90°. It has to be mentioned here that the positions of the main plane 15a, the axis of symmetry 16a and the main axis 12a with respect to one another may vary between wide limits. According to our experiments, the presented version has favourable geometry from the point of view of the application.

Returning now to FIG. 2, it can also be seen that, in addition to the accepting opening 14, the head part also has a fusion opening 17 which extends into the lead-through seat 16, and which also includes the first connection piece 18. The second connection piece 32 of the tightening body 31 of the fixing device 30 conforms to the first connection piece 18. In this case, the first connection piece 18 and the second connection piece 32 form a self-locking thread pair with an appropriate thread pitch. The connector piece 33 is also worked into the tightening body 31 of the fixating device 30, and with its help the fixating device 30 may be easily jammed into the fusion opening 17 of the head part 12. In this case the connector piece 33 is an insert that accepts an "Allen key".

The left hand supporting element 10 in FIG. 2 also shows how the connecting unit 20, consisting of elemental connection strands 21, is fixed into the lead-through seat 16 of the head part 12.

Using the instruments according to the invention following the usual preparation in surgical procedures, firstly, the supporting elements 10 are fixed into the selected vertebrae 41 of the spinal column 40. The threaded stem 11 of the supporting element 10 is screwed into the vertebra 41 so that as small a part as possible of the threaded stem 11 of the supporting element 10 protrudes from the vertebra 41, and so that the head 12 is as close as possible to the surface of the vertebra 41. On screwing in the supporting element 10, the head 12 is set so that the introductory clefts 15 and the lead-through seats 16 are in one direction.

Following this, the elemental connection strands 21 are bent to comply with the position of the heads 12 of the supporting elements 10, and then they are led through the introductory cleft 15 into the lead-through seats 16. When the desired number of elemental connection strands 21 have been fitted into the lead-through seats 16 so that we have produced a connecting unit 20 of the desired "cross-section", then, with the help of the connector pieces 33 and the auxiliary device connected to it, the tightening bodies 31 positioned in the fusion openings 17 of the heads 12 are tightened up.

During tightening, the second connection piece 32, established as a threaded spindle, screws out of the first connection piece 18 that is formed as a threaded sleeve, and the tightening body 31 progresses toward the lead-through seat 16 in the fusion opening 17. During the movement, the tightening body 31 reaches the elemental connection strands 21 run through the lead-through seat 16, presses them against each other and against the delineating walls of the lead-through seat 16 of the head piece 12, and fixes them so that they are immobile in the supporting elements 10. After the connection of all of the supporting elements 10 and the connecting unit 20, a load-bearing structure is formed between the vertebrae 41 of the spinal column 40.

The instrument set according to the invention can be used effectively both for fixating the vertebrae in injuries to the spinal column and for bridging injured vertebrae, independent of whether the operation is to be carried out on the dorsal or lumbar section.

The invention claimed is:

1. A set of surgical instruments for fusing vertebrae, comprising:
supporting elements, each supporting element having a threaded stem that can be screwed into the vertebrae and a head part positioned at an outer end of the threaded stem;
a connecting unit fitted between the supporting elements; and
a fixating device for bracing together the supporting elements and the connecting unit;
wherein the head part of said each supporting element has an accepting opening for receiving and connecting to the connecting unit, the accepting opening being formed by unification of an introductory cleft running from an outer surface of the head part and penetrating into the head part, and a lead-through seat forming a continuation of the introductory cleft, the accepting opening extending into the head part and belling out from there;
wherein the head part has a fusion opening that has a first connection piece and ends in the lead-through seat, the fixating device having a tightening body positioned in the fusion opening so that it is movable, and the tightening body has a second connection piece which operates in unison with the first connection piece;
wherein the connecting unit is assembled from a group of elemental connecting strands that can be moved independently of each other; and
wherein the introductory cleft of the head part has a width which is the same as a width of a single elemental connection strand, while the lead-trough seat has a splayed out cross-section and a width greater than the width of the introductory cleft so that the lead-through seat simultaneously accepts a plurality of elemental connecting strands, and wherein a main axis of the head part forms an angle in a range of 10–120 degrees with a main plane of the introductory cleft.

2. The set of instruments according to claim 1, wherein a longitudinal axis of the threaded stem and the main axis of the head part are coaxially aligned.

3. The set of instruments according to claim 2, wherein an axis of symmetry of the lead-through seat and the main axis of the head part are at an angle in a range of 50–130 degrees with respect to one another.

4. The set of instruments according to claim 3, wherein there is at least one flat area on the outer surface of the head part.

5. The set of instruments according to claim 4, wherein the elemental connecting strands are made of a flexible material that is able to deform.

6. The set of instruments according to claim 3, wherein the elemental connecting strands are made of a flexible material that is able to deform.

7. The set of instruments according to claim 2, wherein there is at least one flat area on the outer surface of the head part.

8. The set of instruments according to claim 7, wherein the elemental connecting strands are made of a flexible material that is able to deform.

9. The set of instruments according to claim 1, wherein a main axis of the head part is at an angle in a range of 10–120 degrees with respect to a main plane of the introductory cleft.

10. The set of instruments according to claim 1, wherein an axis of symmetry of the lead-through seat and a main axis of the head part are at an angle in a range of 50–130 degrees with respect to one another.

11. The set of instruments according to claim 1, wherein there is at least one flat area on the outer surface of the head part.

12. The set of instruments according to claim 1, wherein the elemental connecting strands are made of a flexible material that is able to deform.

13. The set of instruments according to claim 10, wherein there is at least one flat area on the outer surface of the head part.

14. The set of instruments according to claim 13, wherein the elemental connecting strands are made of a flexible material that is able to deform.

15. The set of instruments according to claim 10, wherein the elemental connecting strands are made of a flexible material that is able to deform.

16. The set of instruments according to claim 11, wherein the elemental connecting strands are made of a flexible material that is able to deform.

* * * * *